United States Patent [19]

Petersen et al.

[11] Patent Number: 5,792,330
[45] Date of Patent: Aug. 11, 1998

[54] LANTHANIDE METAL CATIONS FOR CONCURRENT DETECTION AND SEPARATION IN CAPILLARY ELECTROPHORESIS

[75] Inventors: J. R. Petersen, Seabrook; Mohammad Amin Abubaker; M. G. Bissell, both of Galveston, all of Tex.

[73] Assignee: Board of Regents, The University of Texas System, Austin, Tex.

[21] Appl. No.: 457,529

[22] Filed: May 31, 1995

[51] Int. Cl.$^6$ .................................................. G01N 27/26
[52] U.S. Cl. .......................... 204/452; 204/451; 204/602; 204/603
[58] Field of Search ........................ 204/299 R, 180.1, 204/451, 452, 602, 603

[56] References Cited

U.S. PATENT DOCUMENTS

| | | | |
|---|---|---|---|
| 4,352,751 | 10/1982 | Wieder et al. | 260/112 R |
| 4,374,120 | 2/1983 | Soini et al. | 436/546 |
| 4,675,300 | 6/1987 | Zare et al. | 436/172 |
| 4,927,923 | 5/1990 | Mathis et al. | 540/456 |
| 4,935,498 | 6/1990 | Sessler et al. | 534/15 |
| 4,962,045 | 10/1990 | Picozza et al. | 436/501 |
| 5,055,578 | 10/1991 | Hale et al. | 544/209 |
| 5,089,106 | 2/1992 | Karger et al. | 204/299 R |
| 5,089,423 | 2/1992 | Diamandis et al. | 436/518 |
| 5,274,129 | 12/1993 | Natale et al. | 549/349 |
| 5,453,517 | 9/1995 | Kuhn et al. | 549/227 |

FOREIGN PATENT DOCUMENTS

| | | |
|---|---|---|
| 0 064 484 B1 | 7/1986 | European Pat. Off. . |
| 324323 | 7/1989 | European Pat. Off. . |
| 9110908 | 7/1991 | WIPO . |
| WO 91/10908 | 7/1991 | WIPO . |

OTHER PUBLICATIONS

V. M. Mukkala et al., Helvetica Chimica Acta, vol. 75 (1992), 1621–1632.
A. T. Andrews, Electrophoresis 2$^{nd}$ Ed., Clarendon Press, Oxford, 1986, pp. 20 and 117. No month available.
Sigma Catalog, pp. 1689.
M.W.F. Nielen, J. Chromatography, 608 (1992), 85–92 No month available.
Amin et al., "Determination of Steroids in Urine by Micellar HPLC with Detection by Sensitized Terbium Fluorescence," *Analytical Chemistry*, 65(17):2346–2351, Sep. 1993.
Bailey et al., "Terbium Chelate for Use as a Label in Fluorescent Immunoassays," *Analyst*, 109:1449–1450, Nov. 1984.
Bailey and Rocks, "Rapid Spectrofluorometric Determination of Plasma Salicylate with EDTA and Terbium," *Analytica Chimica Acta*, 201:335–338, 1987. No month available.
Burton and Sepaniak, "Analysis of $B_6$ Vitamers by Micellar Electrokinetic Capillary Chromatography with Laser-Excited Fluorescence Detection," *Journal of Chromatographic Science*, 24:347–351, Aug., 1986.
Charles and Riedel, "A Fluorescent Terbium Chelate System in Water Solution," *Journal of Inorganic Nucl. Chem.*, 28:527–536, 1966. No month available.

(List continued on next page.)

*Primary Examiner*—Kathryn Gorgos
*Assistant Examiner*—Alex Noguerola
*Attorney, Agent, or Firm*—Arnold, White & Durkee

[57] ABSTRACT

The present invention provides a method for direct detection concurrently with separation in capillary electrophoresis using a lanthanide cation selected from the group consisting of Tb(III), Eu(III), Dy(III), and Sm(III) to provide fluorescence for enhanced sensitivity. Analytes separated and concurrently detected using this method have an absorption spectrum from about 230 nm to 400 nm and include compounds having an $\alpha,\beta$ unsaturated carbonyl group, an $\alpha$-keto acid, an aromatic moiety, indole carboxylic acid, a diketone moiety, or an organic acid, for example, a salicylic acid, a carboxylic acid, or an amino acid. Advantages of this method include the lack of derivatization, either pre- or post-column, loss of analyte during derivatization is avoided, and fewer items are needed for a commercial capillary electrophoresis kit.

25 Claims, 8 Drawing Sheets

OTHER PUBLICATIONS

Cheng and Dovichi, "Subattomole Amino Acid Analysis by Capillary Zone Electrophoresis and Laser–Induced Fluorescence," *Science*, 242:562–564, Oct. 1988.

Christopoulos and Diamandis, "Enzymatically Amplified Time–Resolved Fluorescence Immunoassay with Terbium Chelates," *Analytical Chemistry*, 64(4):342–346, Feb. 1992.

Cohen et al., "High–Performance Capillary Electrophoretic Separation of Bases, Nucleosides, and Oligonucleotides: Retention Manipulation via Micellar Solutions and Metal Additives," *Analytical Chemistry*, 59(7):1021–1027, Apr. 1987.

Crosby et al., "Spectroscopic Studies of Rare Earth Chelates," *J. Mol. Spectry*, 66:2493–2499, Dec. 1962.

Escabi–Perez et al., "Energy Transfer in Micellar Systems. Steady State and Time Resolved Luminescence of Aqueous Micelle Solubilized Naphthalene and Terbium Chloride," *Journal of the American Chemical Society*, 99(24):7749–7754, Nov. 1977.

Eskola et al., "Time–Resolved Fluoroimmunoassay of Human Pancreatic Phospholipase $A_2$," *Clinical Chemistry*, 29(10):1777–1780, 1983. No month available.

Foret and Boček, "Capillary Electrophoresis: Present State of Art," *Electrophoresis*, 11:661–664, 1990. No month available.

Foret et al., "Separation of Some Triazine Herbicides and Their Solvolytic Products by Capillary Zone Electrophoresis," *Electrophoresis*, 11:95–97, 1990. No month available.

Foret et al., "Capillary Zone Electrophoresis of Rare Earth Metals with Indirect UV Absorbance Detection," *Electrophoresis*, 11:780–783, 1990. No month available.

Gassmann et al., "Electrokinetic Separation of Chiral Compounds," *Science*, 230:813–814, Nov. 1985.

Georges, "Lanthanide–Sensitized Luminescence and Applications to the Determination of Organic Analytes," *Analyst*, 118:1481–1486, Dec. 1993.

Gross and Yeung, "Indirect Fluorimetric Detection and Quantification in Capillary Zone Electrophoresis of Inorganic Anions and Nucleotides," *Journal of Chromatography*, 480:169–178, 1989. No month available.

Guttman and Cooke, "Capillary Gel Affinity Electrophoresis of DNA Fragments," *Analytical Chemistry*, 63(18):2038–2042, Sep. 1991.

Guttman et al., "Prediction of Migration Behavior of Oligonucleotides in Capillary Gel Electrophoresis," *Journal of Chromatography*, 593:297–303, 1992. No month available.

Hemmilä et al., "Europium as a Label in Time–Resolved Immunofluorometric Assays," *Analytical Biochemistry*, 137:335–343, 1984. No month available.

Hernandez et al., "Laser–Induced Fluorescence Detection for Capillary Electrophoresis: A Powerful Analytical Tool for the Separation and Detection of Trace Amounts of Analytes," in: *Capillary Electrophoresis*, Guzman (ed), Marcel Dekker, Inc. N.Y., N.Y., 1993. No month available.

Honda et al., "High–Performance Capillary Zone Electrophoresis of Carbohydrates in the Presence of Alkaline Earth Metal Ions," *Journal of Chromatography*, 588:327–333, 1991. No month available.

Honda et al., "Capillary Zone Electrophoresis of Reducing Mono– and Oligo–Saccharides as the Borate Complexes of Their 3–Methyl–1–Phenyl–2–Pyrazolin–5–One Derivatives," *Carbohydrate Research*, 215:193–198, 1991. No month available.

Issaq et al., "Capillary Electrophoresis Separation of Small Peptides: Effect of ph, Buffer Additives, and Temperature," *Journal of Liquid Chromatography*, 15(6&7):1129–1142, 1992. No month available.

Kuhr and Yeung, "Indirect Fluorescence Detection of Native Amino Acids in Capillary Zone Electrophoresis," *Analytical Chemistry*, 60(17)1832–1834, Sep. 1988.

Jorgenson et al., "Zone Electrophoresis in Open–Tubular Glass Capillaries: Preliminary Data on Performance," *J. High Resolut. Chromatogr. Commun*, 4:230–231, May 1981.

Karovičová et al., "Determination of Nitrates in Vegetables by Capillary Isotachophoresis," *Die Nahrung*, 34:765–767, 1990. No month available.

Kuhr and Yeung, "Optimization of Sensitivity and Separation in Capillary Zone Electrophoresis with Indirect Fluorescence Detection," *Analytical Chemistry*, 60(23):2642–2646, Dec. 1988.

Latva et al., "Time–Resolved Luminescence Detection of Europium(III) Chelates in Capillary Electrophoresis," *Analyst*, 120:367–372, Feb. 1995.

Leung and Meares, "Attachment of Fluorescent Metal Chelates to Macromolecules Using Bifunctional Chelating Agents," *Biochemical and Biophysical Research Communications*, 75(1):149–155, 1977. No month available.

McCormick, "Capillary Zone Electrophoretic Separation of Peptides and Proteins Using Low pH Buffers in Modified Silica Capillaries," *Analytical Chemistry*, 60(21):2322–2328, Nov. 1988.

Miller and Thirkettle, "The Fluorimetric Determination of Transferrin in Blood Serum" *Biochemical Medicine*, 13:98–100, 1975. No month available.

Mosher, "The Use of Metal Ion–Supplemental Buffers to Enhance the Resolution of Peptides in Capillary Zone Electrophoresis," *Electrophoresis*, 11:765–769, 1990. No month available.

Nickerson and Jorgenson, "High Sensitivity Laser Induced Fluorescence Detection in Capillary Zone Electrophoresis," *Journal of High Resolution Chromatography & Chromatography Communications*, 11:878–881, Dec., 1988.

Nishi et al., "Separation and Determination of Lipophilic Corticosteroids and Benzothiazepin Analogues by Micellar Electrokinetic Chromatography Using Bile Salts," *Journal of Chromatography*, 513:279–295, 1990. No month available.

Olefirowicz and Ewing, "Capillary Electrophoresis in 2 and 5 μm Diameter Capillaries: Application to Cytoplasmic Analysis," *Analytical Chemistry*, 62(17):1872–1876, Sep. 1990.

Otsuka et al., "Separation of Aromatic Sulfides by Electrokinetic Chromatography with Micellar Solution," *Nippon Kagaku Kaishi*, 7:950–955, 1986. No month available.

Pettersson et al., "Time–Resolved Fluoroimmunoassay of Human Choriogonadotropin," *Clinical Chemistry*, 29(1):60–64, 1983. No month available.

Schreurs et al., "Determination of Orotate by Liquid Chromatography with Sensitized Lanthanide Ion Luminescence Detection," *Analytica Chimica Acta*, 262:201–208, 1992. No month available.

Siepak, "Terbium Chelate Labels for Fluorescence Immunoassays," *Analyst*, 114:529–531, Apr. 1989.

Siepak, "Use of a Terbium Chelate as Label in Spectrofluorometric Determinations of Protein Traces," *Analytica Chimica Acta*, 218:143–149, 1989. No month available.

Stevenson, "A Critical Review of the Development of HPCE Instrumentation," *American Laboratory*, 26(18):29–33, 1994. No month available.

Swerdlow et al., Three DNA Sequencing Methods Using Capillary Gel Electrophoresis and Laser–Induced Fluorescence, *Analytical Chemistry*, 63(24):2835–2841, Dec. 1991.

Szejtli et al., "Cyclodextrin Use in Separations," *In: Ordered Media in Chemical Separations*, W.L. Hinze and D. W. Armstrong (Eds.), ACS Symposium Series 342, American Chemical Society, Washington, D.C., pp. 200–217, 1987. No month available.

Terabe et al., "Effect of Urea Addition in Micellar Electrokinetic Chromatography," *Journal of Chromatography*, 545:359–368, 1991. No month available.

Terabe et al., "Electrokinetic Separations with Micellar Solutions and Open–Tubular Capillaries," *Analytical Chemistry*, 56(1):111–113, Jan. 1984.

Tobita et al., "The Paramagnetic Metal Effect on the Ligand Localized $S^1 \rightarrow T_1$ Intersystem Crossing in the Rare–Earth–Metal Complexes with Methyl Salicylate," *Journal of Physical Chemistry*, 89(26):5649–5654, 1985. No month available.

Tran and Zhang, "Luminescence Detection of Rare–Earth Ions by Energy Transfer From Counteranion to Crown Ether–Lanthanide Ion Complexes," *Analytical Chemistry*, 62(8):835–840, Apr. 1990.

Wallingford and Ewing, "Amperometric Detection of Catechols in Capillary Zone Electrophoresis With Normal and Micellar Solutions," *Analytical Chemistry*, 60(3):258–263, Feb., 1988.

Weissman, "Intramolecular Energy Transfer: The Fluorescence of Complexes of Europium," *Journal of Chemical Physics*, 10:214–217, Apr. 1942.

Whan and Crosby, "Luminescence Studies of Rare Earth Complexes: Benzoylacetonate and Dibenzoylmethide Chelates," *Journal of Molecular Spectroscopy*, 8:315–327, 1962. No month available.

Wu and Dovichi, "High–Sensitivity Fluorescence Detector for Fluorescein Isothiocyanate Derivatives of Amino Acids Separated by Capillary Zone Electrophoresis," *Journal of Chromatography*, 480:141–155, 1989. No month available.

Nickerson and Jorgenson, "High Speed Capillary Zone Electrophoresis with Laser Induced Fluorescence Detection," *Journal of High Resolution Chromatography & Chromatography Communications*, 11:533–534, 1988. No month available.

Jercan and Popa, "Complex Compounds of Lanthanides with Complexon Type Ligands," *An. Univ. Bucuresti, Ser. Stiint. Natur., Chim*, 18(1):101–111, 1969.

Mikola and Miettinen, "Preparation of Europium–Labeled Derivatives of Cortisol for Time–Resolved Fluoroimmunoassays," *Steriods*, 56:17–21, 1991.

Popa and Jercan, "Electrophoretic Studies Regarding the Stability of Complex Compounds of Lanthanides with Ethylenediaminetetraacetic Acid," *An. Univ. Bucuresti, Ser. Stiint. Natur., Chim.*, 18(1):71–78, 1969.

International Search Report dated Aug. 27, 1996.

5,792,330

1

LANTHANIDE METAL CATIONS FOR CONCURRENT DETECTION AND SEPARATION IN CAPILLARY ELECTROPHORESIS

FIELD OF THE INVENTION

The present invention relates to the field of separation technology, in particular, to capillary electrophoresis and methods for increasing the sensitivity of detection and efficiency of separation of compounds in capillary electrophoresis.

DESCRIPTION OF THE RELATED ART

Sensitive and selective determination of amino acids, polyaminopolycarboxylic acids, organic acids and steroids has always presented a unique analytical challenge. For the majority of clinical, forensic, toxicological and environmental applications, a sensitivity of 1–10 ng/ml is required for these compounds. Radioimmunoassays, although sensitive, are not specific because of the similarity in structures within each family of these compounds. Additionally, radioimmunoassays result in undesirable low level radioactive waste. Therefore, chromatographic techniques with high resolution and sensitive detection are an attractive alternative approach for their determination.

The low volatility, lack of native fluorescence and low absorptivity in the UV-VIS region for these compounds necessitates derivatization so as to make them amenable for either gas chromatography (GC) or high performance liquid chromatographic techniques (HPLC). After derivatization, detection limits in the range of pico- to femtomoles are easily obtained by either GC, GC-MS or HPLC in conjunction with fluorescence detection. This extra step increases the probability of extraneous contamination and results in a longer turn-around time. Thus, a chromatographic method that is devoid of any derivatization steps, but at the same time is highly sensitive, will be indispensable for the routine analysis of these compounds.

The resolution offered by capillary electrophoresis (CE) coupled with shorter analysis times make it a promising technique for the determination of a variety of structurally similar analytes. Numerous modifications, in terms of buffers and detectors, have led to the development of methods that have biological and clinical application such as the separation of amino acids (Jorgensen et al., 1981; McCormick, 1988), oligonucleotides (Guttman et al., 1991; Macek et al., 1992), carbohydrates (Honda et al., 1991a, 1991b), organic acids (Karovicova et al., 1991; Foret et al., 1990) and catecholamines (Olefirowicz et al., 1990; Wallingford et al., 1988).

Resolution and sensitivity are the components of CE that require optimization. The resolution in CE can be enhanced by adding various modifiers, such as urea (Terabe et al., 1991), β-cyclodextrin (Szejtli et al., 1987), organic solvent (Otsuka et al., 1986), detergents (Terabe et al., 1984; Janini et al., 1987) and metals (Cohen et al., 1987), resulting in high efficiencies and excellent separations. However, no such simple solutions are available for enhancing sensitivity, which is the limiting factor in the use of present day commercial CE instruments. Sensitivity is especially problematic in compounds with low molar absorptivity in the ultraviolet and visible regions e.g., amino acids, aliphatic organic acids and polyaminopolycarboxylic acids. The routinely used UV-VIS absorbance detector with specially designed Z and bubble cells can only afford a detection limit in the millimolar range for these compounds and submicromolar range for strongly absorbing compounds (Stevenson, 1994). Fluorescence detection offers a potential of improving the detection limits for these compounds by 100 to 1000 times over UV absorbance. However, an important prerequisite for fluorescence detection is that the compound to be analyzed must be fluorescent or, alternatively, made fluorescent by tagging it with a strong fluorophore which is often a lengthy procedure. Fluorescence detectors with non-laser excitation sources are capable of detection limits in the nanomolar range for strongly fluorescent analytes. Lasers can further extend the detection limits of these compounds by two orders of magnitude ($10^{-11}$M) (Burton et al., 1986; Gassman et al., 1985; Kuhr et al., 1988a, 1988b; Gross et al., 1989; Nickerson et al., 1988a, 1988b; Cheng et al., 1988; and Wu et al., 1989).

Transition metals, such as Zn(II) and Cu(II), enhance resolution of different peptides in capillary electrophoresis (Cohen et al., 1987; Mosher, 1990; Issaq et al., 1992). However, most of the transition metals used for this purpose absorb strongly in the UV-region, thereby causing a high background absorbance, thus resulting in lower sensitivities. Lanthanides, on the other hand, absorb very weakly in the UV region and at the same time are capable of forming both weak and strong complexes with a variety of biologically important ligands (Soini, 1994; Evans, 1990).

The intense fluorescence and longer decay time of the fluorescent complexes of europium (Eu), terbium (Tb), dysprosium (Dy) and samarium (Sm) have resulted in numerous publications (Soini et al.) and patents in the area of time resolved fluoroimmunoassay, especially the DELFIA assay (Hemmilä et al., 1984; Pettersson et al., 1983; Hemmilä et al., 1982; Mikola et al., 1984).

The lanthanide metals belong to a group of fourteen elements that follow lanthanum in the periodic table. They differ from other elements in the periodic table by virtue of having partially filled 4f electronic shells. The 4f electronic configuration plays an important role in the radiative transitions of these elements, particularly when they are complexed with organic ligands such as β-diketones (Soini et al., 1987). The fluorescence quantum yields of uncomplexed lanthanide ions in aqueous media is one hundredth to one thousandth of the fluorescence quantum yield of the best fluorescent organic compound e.g. fluorescein. This is primarily due to their weak absorptivities and non-radiative deactivation by the high energy vibration of the solvent molecules, specifically, the hydroxyl vibrations of water.

The fluorescence quantum yields are dramatically enhanced upon complexing of these ions with suitable organic ligands (Georges, 1993). Weissman (1942) concluded that excitation light is absorbed by the organic part of a lanthanide complex and emitted as the line spectrum of the lanthanide ion. The energy transfer mechanism published by Crosby et al. (1962) is illustrated in FIG. 1. Typically, it involves energy absorption by the organic part of the complex (ligand), leading to its excitation from the ground singlet state, $S_0$, to one of the excited states, $S_1$. At this stage, there are two alternative routes available. The molecule can either deactivate by radiative transition from $S_1$ to $S_0$ (prompt ligand fluorescence), or undergo transition to one of the triplet states, T. From the triplet state, the molecule can return to the ground state by means of spin-forbidden transition ($T \rightarrow S_0$) (molecular phosphorescence) or the energy can be transferred to the central lanthanide ion. Essentially, this process consists of transfer of energy from the triplet state of the ligand to some appropriate 4f level of lanthanide. When receiving energy from the triplet states, the lanthanide ion comes to the resonance state and can undergo radiative transition resulting in the characteristic line emission of the ion (ion fluorescence). The latter is a special feature of the lanthanide chelates, which has no parallel in either the fluorescence or the phosphorescence of organic molecules.

The formation of a complex between a suitable organic donor and a lanthanide ion is not required for efficient energy transfer. It has been reported that an efficient transfer of energy can be achieved by sequestering the donor and acceptor inside a micelle (Mohammad et al., 1993; Escabi-Perez et al., 1977). This type of energy transfer (termed Förster energy transfer) results from collisional interaction between a donor and acceptor molecule, and the transfer efficiency is inversely proportional to the distance between the two molecules. The luminescence intensity of sensitized lanthanide ions depends on two factors (Soini et al., 1987; Whan et al., 1962; Tobita et al., 1985). First, the efficiency of energy transfer depends on the matching between the triplet level of the organic compound and the resonance level of the ion; the energy of the triplet level should be close to, but no lower than, the resonance level of the lanthanide ion. Second, the probability of non-radiative deactivation of the resonance level of the lanthanide ion should be as low as possible when compared to that of the radiative transition. Numerous organic ligands and assay protocols have been reported to fulfill these requirements, resulting in a strong enhancement in terbium ion fluorescence (Kallistratos et al., 1982).

Energy transfer to lanthanides can occur when more than one ligand associates with terbium to form a ternary complex in aqueous medium. In this complex, the lanthanide acts as an acceptor and one of the ligands acts as a donor. Charles et al. (1966) reported an efficient energy transfer from sulfosalicylic acid to terbium in a sulfosalicylic acid —Tb(III)-ethylenediamine tetraacetic acid ternary complex. The phenomenon was later applied to the determination of a variety of compounds ranging from salicylic acid to proteins in serum by time resolved fluoroimmunoassays (Eskola et al., 1983; Siepak, 1989a; Leung et al., 1977; Bailey et al., 1984; Siepak, 1989b; Bailey et al., 1987; Miller et al., 1975; Christopoulos, 1992). The specificity for different compounds was imparted by using monoclonal or polyclonal antibodies and separating the antigen-antibody complex prior to detection.

Although the application of lanthanides in fluoroimmunoassay is well documented, their utility in chromatographic or electrophoretic separation and detection is relatively unexplored. Terbium was reportedly used for postcolumn detection and quantitation in high pressure liquid chromatography to detect either orotate or steroids possessing an α,β-unsaturated carbonyl group (Mohammad et al., 1993; Schreurs et al., 1992). Nielen (1992) reported the feasibility of using an acetylacetonate complex of terbium for the determination of anions such as, nitrite, chromate, hexacyanoferate (II) and (III), using the dynamic quenching of time-resolved luminescence of the terbium (III)-acetylacetone chelate for indirect detection in CZE. A sensitivity in the range of ppb for nitrite is reported by these authors.

The separation of steroids by micellar electrokinetic capillary electrophoresis (MEKC) has always been problematic. MEKC with sodium dodecyl sulfate (SDS) has been unsuccessful in separating steroids, because steroids migrate with almost the same velocity as that of the SDS micelle, owing to their high lipophilicity. The separation could be achieved only after addition of certain organic modifiers such as bile acid (Nishi et al., 1990).

Because of all of the above problems associated with resolution and sensitivity, current capillary electrophoretic procedures are not completely satisfactory, and persons skilled in the art have searched for improvements.

SUMMARY OF THE INVENTION

The present invention seeks to overcome these and other drawbacks inherent in the prior art by providing a method for direct detection concurrently with separation in capillary electrophoresis using certain lanthanide cations to provide fluorescence for enhanced sensitivity. Advantages of this method include the lack of derivatization either pre- or post-column which means that loss of analyte during derivatization is avoided, and fewer items are needed for a commercial kit.

The present invention provides a method of separating and concurrently detecting an organic analyte having an absorption spectrum from about 230 nm to 400 nm in a sample. The method comprises applying a voltage to a capillary electrophoresis apparatus that contains the sample, or a portion thereof, in the presence of a lanthanide cation selected from the group consisting of Tb(III), Eu(III), Dy(III), and Sm(III) in an amount sufficient to complex with the analyte, to electrophoretically separate the analyte of the sample, and concurrently detecting the separated analyte by measuring lanthanide ion fluorescence resulting from photoexcitation of the analyte.

The organic analyte, having an absorption spectrum from about 230 nm to 400 nm, may have an excited energy level sufficient to transfer energy directly to the lanthanide cation. The excited energy level sufficient to transfer energy to each of these lanthanide cations is greater than or about the $^4G_{5/2}$ level for Sm(III), $^5D_0$ for Eu(III), $^5D_4$ for Tb(III), or $^4F_{9/2}$ level for Dy(III). Examples of these organic analytes include analytes having an α,β unsaturated carbonyl group, an α-keto acid, an aromatic group, an indole carboxylic acid, a β-diketone group, a pyrrole, furan, thiophene, phenyl, biphenyl, pyridine, pyrimidine, pyrazine, quinoline, phenanthroline, purine, porphyrin or a phosphonimido moiety. Particularly preferred organic analytes having an excited energy level sufficient to transfer energy directly to the lanthanide cation include salicylic acid, p-aminosalicylic acid, sulfosalicylic acid, indole carboxylic acid, testosterone, mesterone, bolasterone, cortisone, progesterone, hydrocortisone, corticosterone, or fluoxymesterone.

In some embodiments, the wavelength for photoexcitation of the analyte is not readily achievable, and although the analyte has an excited energy level sufficient to transfer energy to the lanthanide cation, it is desirable in these embodiments for the applying step to be further carried out in the presence of a molecule capable of forming a ternary complex with the lanthanide cation and the analyte to facilitate energy transfer for ease of photoexcitation and detection. Examples of such an analyte is an amino acid; or a polycarboxylic acid, such as ethylenediamine tetraacetic acid (EDTA), ethyleneglycol-bis-(β-aminoethylether)-N,N, N'N'-tetraacetic acid (EGTA), citric acid, 1,2 diaminopropane tetraacetic acid, trans-1,2 cyclohexane diaminetetraacetic acid or hexamethylene diaminetetraacetic acid.

In a further embodiment, the organic analyte may not have an excited energy level sufficient to transfer energy directly to the lanthanide cation, and in this embodiment, the applying step is further carried out in the presence of a molecule capable of forming a ternary complex with the lanthanide cation and the analyte to facilitate energy transfer to the lanthanide cation. Examples of such an organic analyte is a crown ether or a cyclodextran, for example, 18 crown 6, 15 crown 6, or an α, or β cyclodextran, and the like.

A molecule capable of forming a ternary complex with the lanthanide cation and the analyte to facilitate energy transfer to the lanthanide cation may have an α,β unsaturated carbonyl group, an α-keto acid, an aromatic group, an indole carboxylic acid, or a β-diketone group. Specific examples of such a molecule are EDTA, EGTA, citric acid, orotate, benzoic acid, salicylic acid, p-aminosalicylic acid, sulfosalicylic acid, or indole carboxylic acid. "Capable of forming a ternary complex" means that the molecule interacts with the lanthanide cation and the analyte to form a stable complex under conditions effective to promote energy transfer to the lanthanide cation.

In the above described methods, preferably, the lanthanide cation is Tb(III) or Eu(III), and most preferably, the lanthanide cation is Tb(III). Europium is the preferred cation for the analysis of aromatic β-diketones, whereas terbium is preferred for the analysis of aliphatic β-diketones. An amount of lanthanide cation sufficient to complex with the analyte is an amount equal to or greater than the molar concentration of the analyte.

Where the electrophoresis is carried out at a pH at which the lanthanide cation may not be soluble, such as a pH value greater than about 7, the applying step is further carried out in the presence of an agent for solubilizing the lanthanide cation. Exemplary solubilizing agents include EDTA, EGTA, citric acid, 1,2 diaminopropane tetraacetic acid, trans-1,2 cyclohexane diaminetetraacetic acid or hexamethylene diaminetetraacetic acid. A preferred solubilizing agent is EDTA.

The applying step may further be carried out in the presence of a running buffer and/or a sample buffer, and the running buffer and/or the sample buffer may be morpholinoethanesulfonic acid (MES), morpholinopropanesulfonic acid (MOPS), tris(hydroxymethyl)-aminomethane (Tris)-citric acid, 4-(2-hydroxyethyl)-1-piperazine ethanesulfonic acid (HEPES), EDTA, sodium carbonate with EDTA, citric acid or boric acid. In addition, the applying step may further be carried out in the presence of a micellar medium, such as dodecyl trimethylammonium bromide (DTAB), SDS, α-[4-(1,1,3,3-tetramethylbutyl)phenyl]-ω-hydroxypoly(oxy-1,2-ethanediyl) (Triton X), polyoxyethylene (20) sorban monolaurate (Tween), or polyoxyethylene (23) lauryl ether (Brij-35).

The detecting may be carried out by laser-induced luminescence or time-resolved luminescence. Excitation of the lanthanide ion may be by a laser, such as a HeCd or KrF laser; by a xenon, deuterium, or mercury lamp; or by a diode laser. The excitation wavelength depends upon the absorption spectrum of the analyte and is independent of binding of the analyte to the lanthanide cation.

A further embodiment of the present invention provides a method of separating and concurrently detecting an organic analyte having an absorption spectrum from about 230 nm to 400 nm in a sample. This method comprises applying a voltage to a capillary electrophoresis apparatus that contains the sample, or a portion thereof, in the presence of Tb(III) to electrophoretically separate the analyte of the sample, and concurrently detecting the separated analyte by measuring terbium fluorescence resulting from photoexcitation of the analyte.

Another embodiment of the invention is a method for detecting an inborn error of metabolism where an organic acid is present in excess in a subject having the inborn error of metabolism. The method comprises the steps of obtaining a sample from the subject, analyzing the sample for the presence of the organic acid using a capillary electrophoretic analysis system comprising a lanthanide cation selected from the group consisting of Tb(III), Eu(III), Dy(III), and Sm(III), and concurrently detecting the organic acid by measuring lanthanide ion fluorescence resulting from photoexcitation of the organic acid. The presence of the organic acid in excess of a control level indicates an inborn error of metabolism. An example of an inborn error of metabolism is phenylketonuria, and in that case, the organic acid is phenylalanine. A control level is the average level of organic acid found in subjects not having the inborn error of metabolism. A preferred sample is a blood or urine sample and a preferred cation is terbium.

A major use of the present invention is expected to be the analysis of bodily samples from athletes who are suspected of having taken an illicit steroid. Therefore, another embodiment of the invention is a method for detecting the presence of an illicit steroid in such a subject. This method comprises the steps of obtaining a sample from the subject, and analyzing the sample for the presence of the steroid using a capillary electrophoretic analysis system comprising a lanthanide cation selected from the group consisting of Tb(III), Eu(III), Dy(III), and Sm(III), and concurrently detecting the presence of the steroid by measuring lanthanide ion fluorescence resulting from photoexcitation of the steroid. Examples of illicit steroids are testosterone, bolasterone, methyltestosterone, or testosterone acetate, and the like. The sample may be any significant bodily fluid, such as blood, urine, saliva, ascites, peritoneal, vitreous humor, or sweat. A preferred sample is a blood or urine sample and a preferred cation for this method is Tb(III).

Another embodiment of the present invention is a kit for capillary electrophoretic separation and concurrent detection of an organic analyte having an absorption spectrum from about 230 nm to 400 nm from a sample. The kit may comprise in packaged combination; i) a carrier means adapted to receive at least 2 container means in close confinement therewith, ii) a first container means including a lanthanide cation selected from the group consisting of Tb(III), Eu(III), Dy(III), and Sm(III); and iii) a second container means including a capillary electrophoresis tube. The concentration of cation may be between about $10^{-4}$M to 1M. The kit may further comprise a third container means including a molecule capable of forming a ternary complex with the lanthanide cation and the analyte to facilitate energy transfer between the analyte and the lanthanide cation. Alternatively, or additionally, the kit may further comprise a container means including a buffer, the buffer may be a concentrate, and that container means may be the first container means. Additionally, the kit may further comprise a third container means including a chelator compound. Preferably, the lanthanide cation is Tb(III), and the molecule capable of forming a ternary complex with the lanthanide cation and the analyte to facilitate energy transfer is a salicylic acid.

The capillary electrophoresis apparatus used in the methods of the present invention includes a capillary tube that may be made of fused silica, a liquid gel or TEFLON™; may be coated with polysiloxane, a C18 or a C4 polymer; and may be disposable.

The methods of the present invention allow analyses for the presence of steroids in blood or urine samples in a fast, effective, and inexpensive manner. Current methods are long, involved, expensive and not specific. For example, in a current diagnostic method for congenital adrenal hyperplasia (CAH), 17-hydroxyprogesterone requires extraction to remove cross-reactive steroids in order to confirm whether an elevated level is real. The present methods allow for diagnosis of CAH or renal hyperplasia in a single analysis.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

DETAILED DESCRIPTION OF THE PREFERRED EMBODIMENTS

The present invention provides for the use of fluorescence from a lanthanide selected from the group consisting of Tb(III), Eu(III), Dy(III), and Sm(III) complexed with an organic analyte, the organic analyte having an absorption spectrum from about 230 nm to 400 nm, for concurrent separation and detection of the analyte without any prior derivatization in capillary electrophoresis. An important feature of this system is maintaining high resolution and sensitivity while eliminating the need of pre- or postcolumn derivatization.

Figure 1:
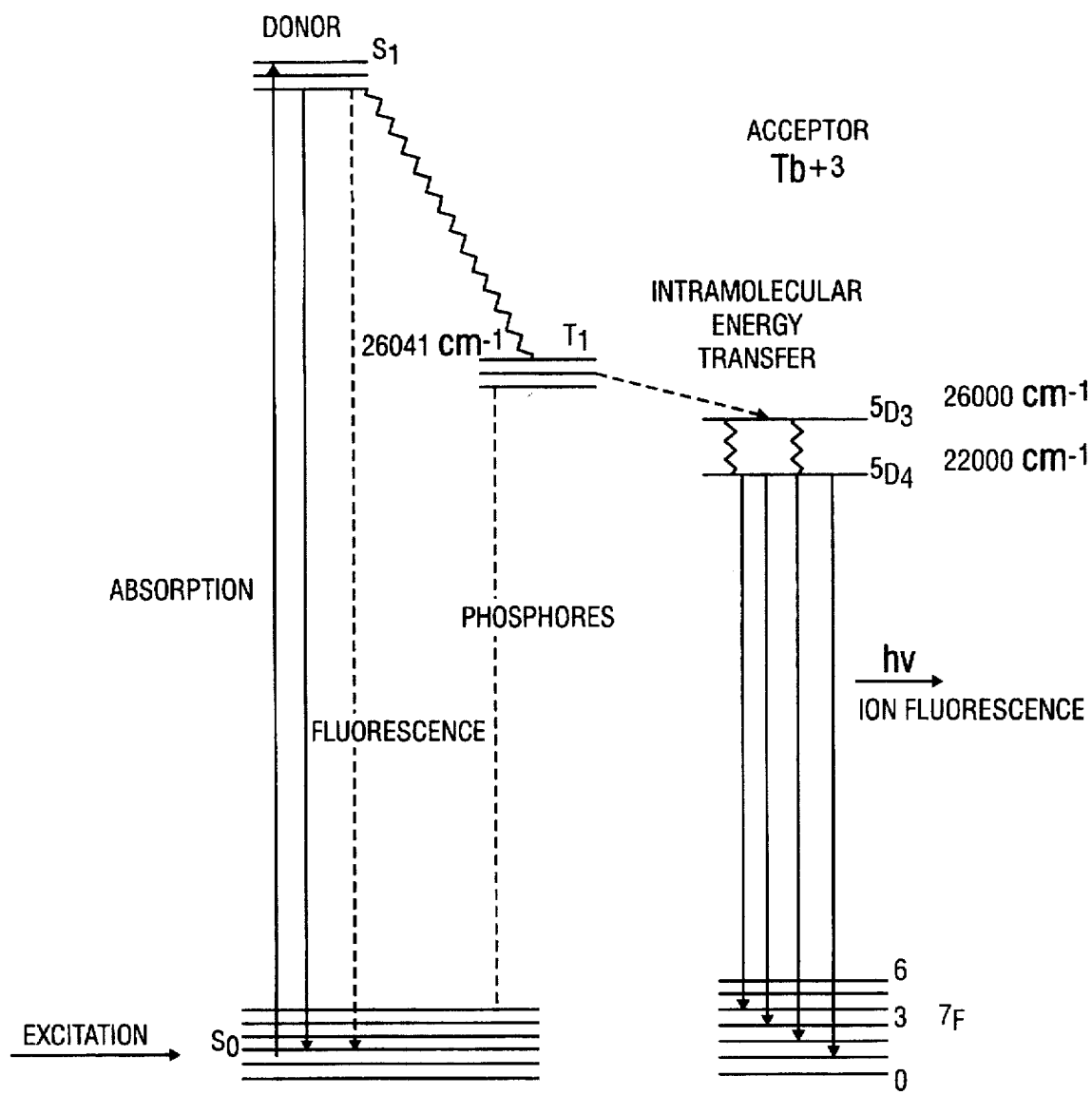
FIG. 1 schematically illustrates an energy transfer mechanism that includes absorption by a ligand leading to excitation from $S_0$ to $S_1$, transition to a triplet state, then to a lanthanide cation which gives fluorescence.

Some organic analytes have an excited energy level sufficient to transfer energy to the lanthanide cation directly. These analytes have a triplet energy state greater than or about the $^4G_{5/2}$ level for Sm(III), $^5D_0$ level for Eu(III), $^5D_4$ for Tb(III), or $^4F_{9/2}$ level for Dy(III). The excitable energy levels of these four lanthanide cations are different and therefore the energy transfer efficiency from an organic analyte depends on the difference between the excited level of the analyte and excitable energy levels of the lanthanide cations, as shown in FIG. 1 for terbium. Such analytes have functional groups such as an $\alpha$, $\beta$ unsaturated carbonyl, an aromatic moiety, a carboxylic acid, or $\beta$-diketone, and include, for example, steroids, salicylates, indole carboxylic acid and aromatic amino acids. The triplet state energy level of a compound may be found in "Systematics and the Properties of the Lanthanides" (ed. Sinha, NATO ASI series, Reidel Publishing Co., Boston, 1982).

An example of the mechanism is as follows. Steroids containing an $\alpha$, $\beta$-unsaturated carbonyl group can transfer energy very efficiently to Tb(III) and Eu(III) cations, when excited at 240 nm. This is because the first excited singlet level of these steroids occurs at 41,666 cm$^{-1}$, corresponding to the absorption at 240 nm, however, it also possesses a triplet level at 26,041 cm$^{-1}$. Therefore, the photophysical phenomena can be envisaged as the radiative excitation of the steroid to the first excited singlet state (i.e. 41,666 cm$^{-1}$), followed by the intersystem crossing to the triplet state (occurring at 26,041 cm$^{-1}$) with subsequent transfer of energy from the triplet level of the steroid to the $^5D_3$ level of terbium (occurring at 26,000 cm-1).

This mechanism holds true for steroids possessing an $\alpha$, $\beta$-unsaturated carbonyl group, and also applies to compounds like salicylic acid or 4-aminosalicylic acid, which absorb light at 325 nm, and then directly transfer energy to terbium by going through an intersystem crossing stage to a triplet state. Generally speaking, in order to have efficient transfer of energy from any organic compound to a lanthanide cation, the excited energy level of organic donor should be in close proximity and greater than $^4G_{5/2}$ level for Sm(III), $^5D_0$ for Eu(III), $^5D_4$ for Tb(III) and $^4F_{9/2}$ level for Dy(III).

Where the analyte to be separated and detected lacks an excited energy level sufficient to transfer energy directly to a lanthanide cation, then a molecule capable of forming a ternary complex with the analyte and the lanthanide cation to facilitate energy transfer is included in the buffer. A molecule capable of forming a ternary complex with the analyte and the lanthanide cation to facilitate energy transfer has an excited energy level sufficient to transfer energy to a lanthanide cation selected from the group consisting of Tb(III), Eu(III), Dy(III), and Sm(III), as described above. Salicylates, indole carboxylic acid, and quinoline are examples of such a molecule. After excitation of the complex, energy absorbed by the salicylate is transferred to the lanthanide ion by the internal energy transfer process. The excited lanthanide ion subsequently fluoresces at its characteristic wavelength which occurs at 488, 547, and 596 nm. A similar type of energy transfer is observed for other lanthanides such as Eu(III), Dy(III), and Sm(III), however, with reduced efficiencies. The quantum efficiency of Gd(III) is low and is expected to be inefficient in the present process, and lanthanum is believed to be unsuitable for use in the present invention since it has intrinsic fluorescence and will not accept energy from other compounds.

For certain analytes and certain pH values, a chelator is necessary for solubilizing the lanthanide cation. For example, the aminopolycarboxylic acid ligand, EDTA, serves to chelate Tb(III) to keep it soluble in water at a strongly alkaline pH, e.g. pH 11–12. Any polyacid that can strongly complex the lanthanide cation is contemplated in the present invention, further examples are EGTA and citric acid.

The running buffer or sample buffer is chosen depending upon the analyte and should possess the following properties.

i) The buffer should solubilize the lanthanide cation at the operational pH for electrophoresis, e.g., EDTA is able to solubilize Tb(III) even at pH=12 by forming an EDTA-Tb(III) complex (Tb will precipitate as Tb(OH)$_3$ at a pH value greater than about 7).

ii) The buffer should permit efficient energy transfer from the analyte to the lanthanide cation, or within a ternary complex formed by the analyte, the lanthanide cation and a molecule facilitating energy transfer. Alternatively, the buffer may serve to compartmentalize terbium and a suitable analyte such as a steroid containing an $\alpha$, $\beta$-unsaturated carbonyl group into a micelle, thereby allowing energy transfer by diffusive encounter. An example of this type of buffer is one containing SDS.

iii) The buffer should prevent quenching of the lanthanide fluorescence by removing water from the coordination sphere of the lanthanide cation.

iv) The buffer should be non-fluorescent or, if fluorescent, the excitation and emission wavelengths should not overlap with that of the lanthanide cation.

v) The buffer should not absorb significantly in the region where the donor molecule is absorbing or, if it does absorb light, is not capable of transferring its energy to a lanthanide cation.

vi) The buffer should be compatible with capillary electrophoresis, i.e., water soluble, low electrophoretic mobility, having minimum joule heating, etc.

Taking all these conditions into consideration, the following buffers are most suitable for different pH ranges: MES (morpholinoethanesulfonic acid) and MOPS (pH range 6–7), Tris in combination with citric acid or HCl (pH 2–9), HEPES (pH 5–7), EDTA (pH 2–14), Na$_2$CO$_3$ in combination with EDTA (pH 8–14), citric acid or boric acid (pH<7) in concentrations from about 1 mM to about 0.2 or 0.3M. "Running buffer" is meant to include both the anode and the cathode buffer. Preferably, the concentration of the running buffer is from about 10 mM to about 200 mM. Most preferably, the running buffer is Tris-HCl at about 10 mM.

A further important aspect of this invention is the role of certain lanthanide cations in enhancing resolution of different steroids in micellar electrokinetic capillary chromatography. In the present method described in Example 3, terbium chloride was added to a buffer containing dodecyltrimethylammonium bromide (DTAB) and trioctylphosphine oxide (TOPO). In the presence of terbium, a complete resolution of eight closely related steroids was achieved, whereas a buffer in which sodium chloride replaced terbium chloride failed to achieve resolution.

Sodium dodecyl sulfate (SDS), TRITON X, TWEEN-20, BRIJ 35, DTAB, and other neutral, anionic, or cationic detergents may be added to the run buffer to facilitate separation or enhance energy transfer efficiency by the process of compartmentalization or to prevent water quenching. All these detergents form micelles. A preferred micellar medium is SDS.

The capillary electrophoresis apparatus comprises a capillary tube made from fused silica, surface modified fused silica (e.g., eCAP™ by Beckmann Instruments, Fullerton, Calif.), polysiloxane coated capillaries (J & W Scientific, Folsom, Calif.), liquid gel inclusion capillaries (Beckmann Instruments), Teflon® capillaries, or capillaries packed with C-8, C-18, etc. coated silica particles. The main advantages of using a coated capillary is in achieving better resolution. The coating on the capillaries is used to modify the electroosmotic flow (EOF), i.e., to eliminate it, to reverse it, or to eliminate interaction of the analytes.

The various modes of capillary electrophoresis (micellar electrokinetic capillary electrophoresis, capillary zone electrophoresis, isotachophoresis, isoelectric focusing, capillary gel electrophoresis) can be made compatible with the present invention. A reference booklet published by Beckman Instruments, Inc. (Fullerton, Calif., 1991) entitled, "Introduction to Capillary Electrophoresis" is specifically incorporated by reference herein for those techniques.

The components of a kit will depend upon the analyte to be separated and detected. Preferably, a kit may contain a suitable capillary to perform electrophoresis and a suitable lanthanide cation. In addition, a kit may contain a buffer, possible in concentrate form, for the running or sample buffer, or both. Alternatively, a running buffer may contain a lanthanide cation or may contain a suitable molecule capable of forming a ternary complex with the analyte and the lanthanide cation to facilitate energy transfer such as salicylic acid. A kit may further comprise a chelator compound or standard molecules for separation to standardize an electropherogram.

The laser-induced photoexcitation and detection methods used in the present invention are known to those of skill in this art in light of the present disclosure. A chapter authored by Hernandez et al. (1993) is incorporated by reference herein for these methods.

Steroids separated in the following examples include: 4-pregnene-17$\alpha$,21-diol-3,11,20-trione (cortisone), hydrocortisone, testosterone, 7$\alpha$-17-dimethyl testosterone, 4-pregnene-11$\beta$,17$\alpha$-diol-3,20-dione (corticosterone), 4-pregnene-3,20-dione (progesterone), 9$\alpha$-fluoro-11$\beta$-hydroxy-17$\alpha$-methyltestosterone (Fluoxymesterone) and testosterone propionate.

Aromatic carboxylic and amino acids separated and detected include salicylic acid (SA), sulfosalicylic acid (SSA), p-amino salicylic acid (PAS), 5-hydroxyindole carboxylic acid (HICA) and phenylalanine. Sodium dodecyl sulfate (SDS) and dodecyltrimethylammonium bromide (DTAB) based buffers were used for micellar electrokinetic capillary electrophoresis.

In the following examples, CE analysis was performed on Beckmann P/ACE 5010 capillary electrophoresis system (Beckmann Instruments Inc., Fullerton, Calif.) equipped with system Gold software for data analysis. A fixed UV wavelength at 254 nm was employed for absorbance detection. An Omnichrome-Series 39, 325 nm Helium Cadmium (HeCd) laser was used for excitation and a Beckmann LIF (laser induced fluorescence) detector was used for luminescence detection. A KrF laser may be used also (Omnichrome, Inc., Chino, Calif.).

Separations were performed in 50 μm I.D.×375 μm O.D. fused silica or polyacrylamide coated neutral capillary tubes (Beckmann Instruments Inc., Fullerton, Calif.). The size of the capillary will vary depending on the separation requirements. The I.D. may be from about 5–200 μm. The length of capillary is dictated by the separation desired and the invention can be made compatible for micro capillaries etched on 1×1 cm silicon chips, as well as capillaries having over 100 cm of length. In some cases, samples may be well separated on a 20 or 25 cm capillary, however, for analytes having similar properties, a longer capillary may be used, for example, a capillary of 45–50 cm. For specifics regarding a description of the components and operation of capillary electrophoresis systems, see, for example Swerdlow et al., U.S. Pat. Nos. 5,259,939 and 5,264,095, which references are incorporated herein by reference. A temperature of 16°±0.2° C. was maintained in all separations.

Although the invention is described in detail with reference to the separation of steroids in micellar medium and separation and detection of ternary complexes formed by different salicylates with Tb-EDTA in CE, it is to be understood that the invention applies equally to the ternary complexes of Eu(III), Sm(III), and Dy(III), particularly to Eu(III), and to the resolution enhancement mediated by these lanthanides. The invention includes those situations where enhancement in luminescence from these lanthanide complexes results either by complex formation or by Förster type of energy transfer used in conjunction with capillary electrophoresis.

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention. Accordingly, it is intended that all such alternatives, modifications, and variations which fall within the spirit and the scope of the invention be embraced by the defined claims.

EXAMPLE 1

Figure 2:
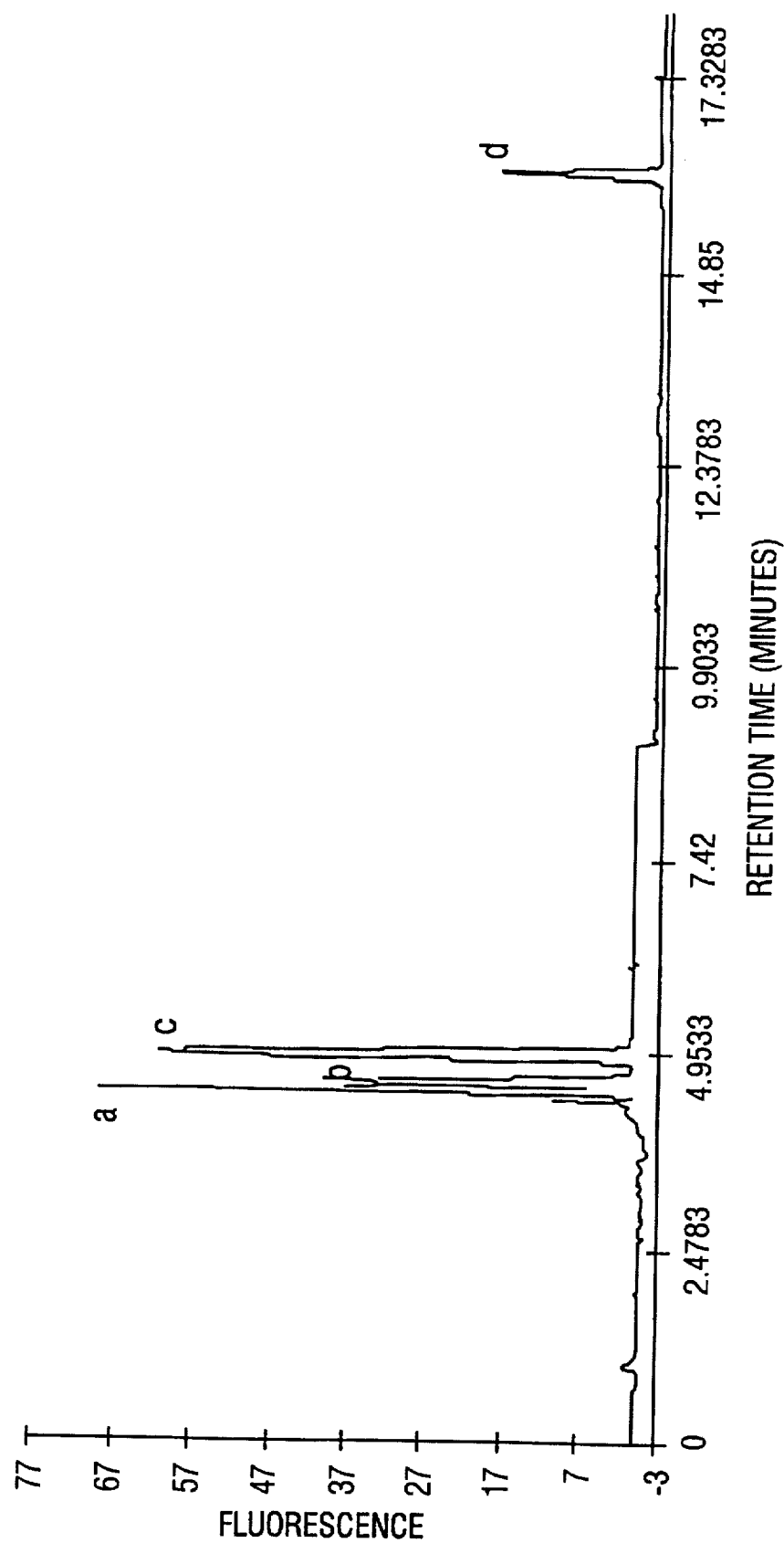
FIG. 2 depicts a typical electropherogram separating 5-hydroxyindole carboxylic acid (a), p-aminosalicyclic acid (b), salicylic acid (c), and sulfosalicylic acid (d).

Separation and Detection of Salicylates by CE via Laser-Induced Luminescence The present example provides for concurrent separation and detection of analytes having excited energy levels sufficient to transfer energy directly to a lanthanide cation of the present invention, by CE via laser induced luminescence. A typical electropherogram separating 5-hydroxyindole carboxylic acid (a), p-aminosalicyclic acid (b), salicylic acid (c), and sulfosalicylic acid (d) is shown in FIG. 2. This separation was performed in a 50 cm long (injector to detector), 50 µm I.D.×375 µm O.D. fused silica capillary tube (Beckmann Instruments Inc., Fullerton, Calif.). The running buffer was 1 mM EDTA-Tb(III) chelate and 10 mmol Tris-HCl buffer at pH 11.07. The electrophoresis was performed by applying 30 kV voltage across the electrodes. The separated components were detected by laser induced luminescence. The sample prepared in 10 mmol Tris-HCl buffer with pH adjusted to 11 by 0.1N NaOH was hydrodynamically injected for 10 seconds.

At the pH of this separation, EDTA is present to keep Tb(III) soluble. Under these conditions, the salicylates and indole carboxylic acid form a ternary complex with EDTA-Tb(III) chelates which are subsequently separated by electrophoresis. The formation of ternary complexes permits an efficient energy transfer from aromatic rings to the central lanthanide ion upon excitation by 325 nm HeCd laser. A detection limit in the range of $1 \times 10^{-7}$ M was achieved.

Figure 5:
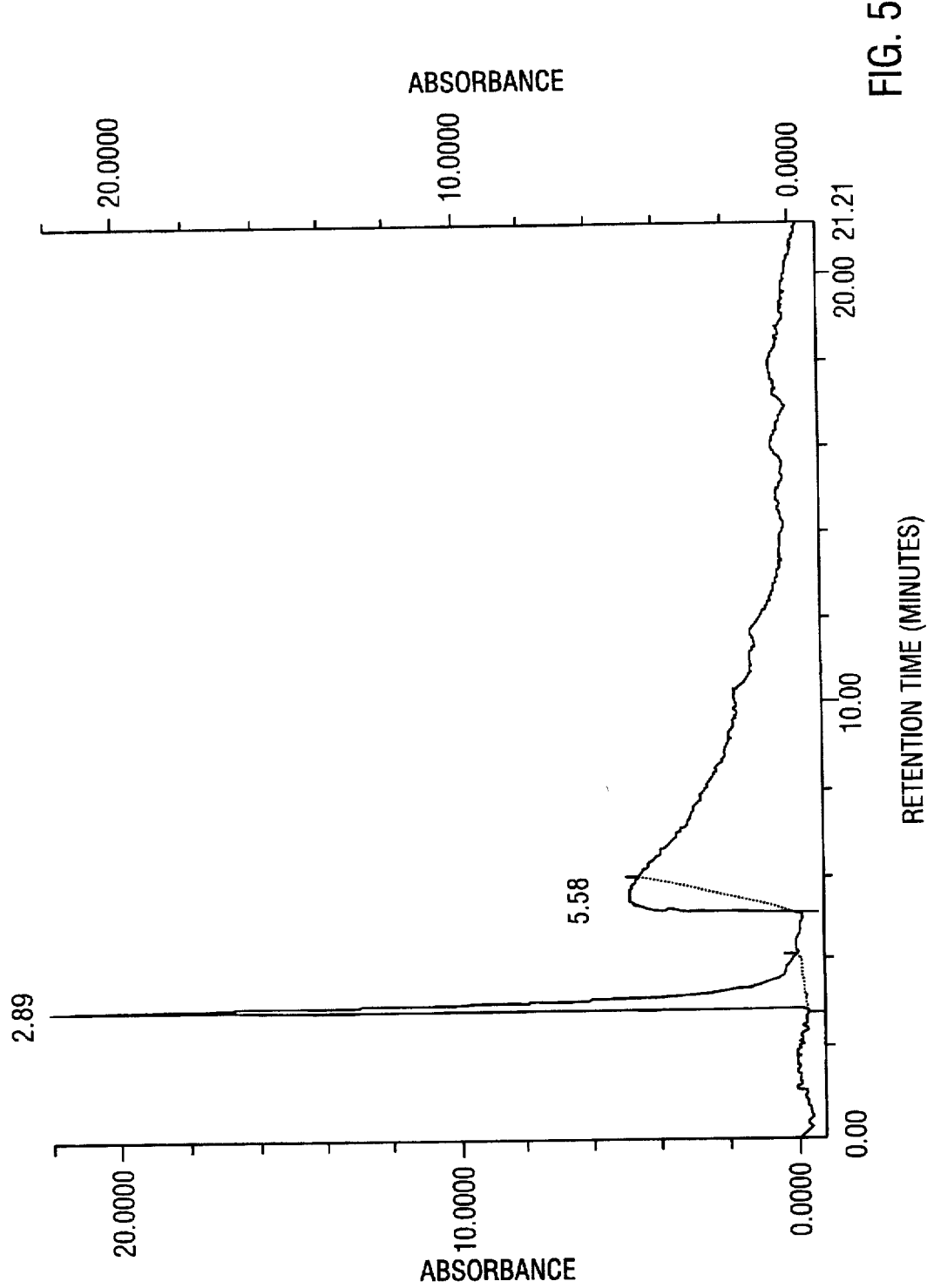
FIG. 5 demonstrates the separation of salicylic acid (retention time of 2.89 min) and sulfosalicylic acid (retention time of 5.58 min) without a chelator in the buffer at low pH.

The separation of salicylic acid and sulfosalicylic acid without the presence of a chelator at low pH is shown in FIG. 5. The buffer was 20 mM MOPS (pH=6) with 0.01M $TbCl_3$, electrophoresis was at 30 kV at 16° C. At low pH, the acids are deprotonated and chelate Tb(III) without the addition of a chelator.

EXAMPLE 2

Amino Acid Separation and Detection

Figure 3:
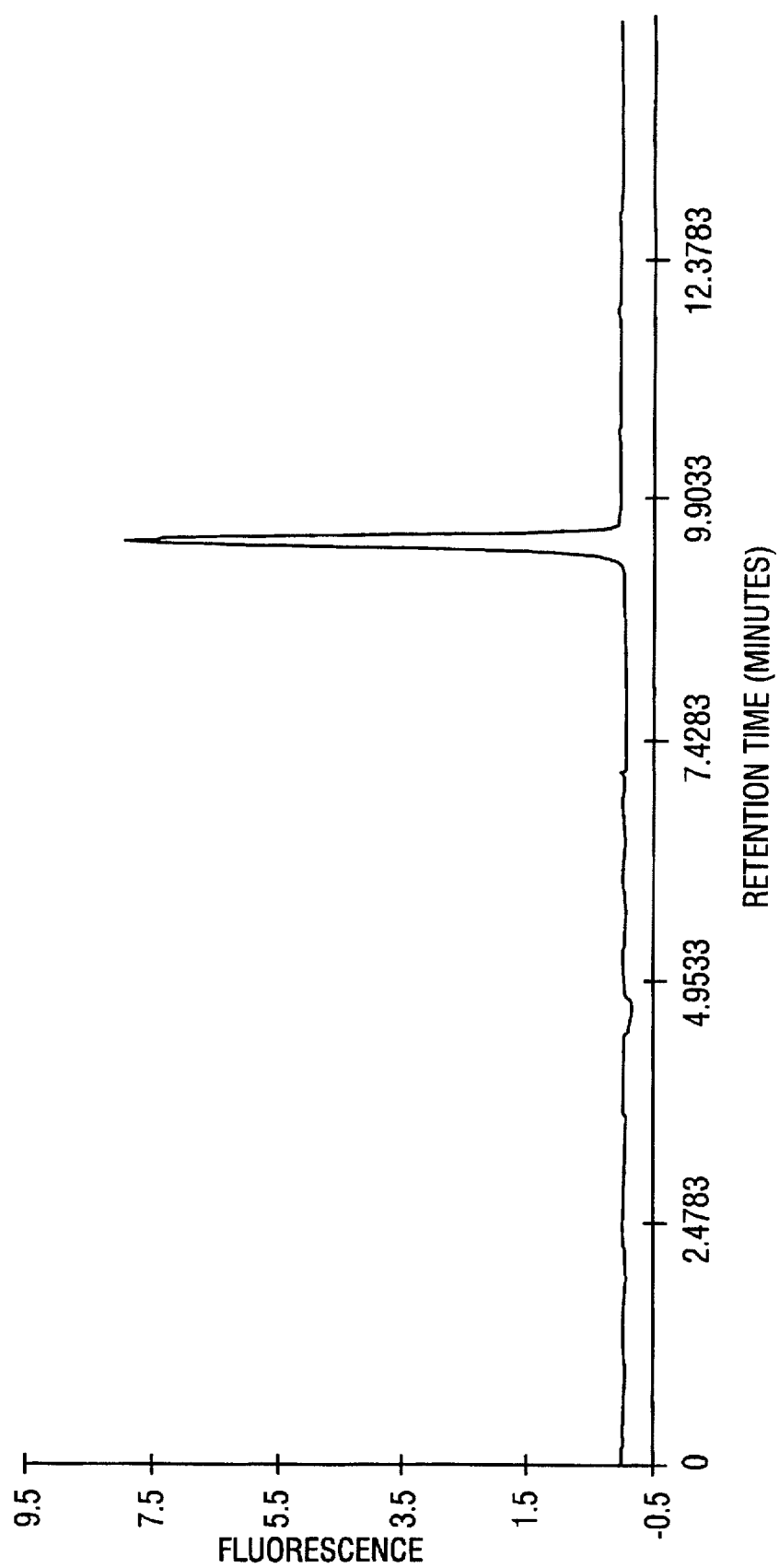
FIG. 3 shows a ternary complex of phenylalanine-Tb-EDTA that provided a detection limit in the submicrogram range ($1 \times 10^{-7}$M). The concentration of phenylalanine was $1.0 \times 10^{-6}$M.

The present example demonstrates the separation and detection of an amino acid, phenylalanine, a molecule that is able to transfer energy directly to a lanthanide cation due to its phenyl moiety. A ternary complex formed with phenylalanine-Tb-EDTA yielded a detection limit in the sub micromole range ($1 \times 10^{-7}$ M) as shown in FIG. 3.

EXAMPLE 3

Separation of Steroids Containing α,β Unsaturated Carbonyl Groups

The present example demonstrates the separation of further molecules having an excited energy state sufficient to transfer energy directly to Tb(III).

The separation of eight steroids containing α,β unsaturated carbonyl groups was carried out in a 50 cm (injector to detector), 50 µm I.D.×375 µm O.D. fused silica capillary tube (Beckmann Instruments Inc., Fullerton, Calif.). The running buffer consisted of 50 mM DTAB, 5.2 mM trioctylphosphine oxide and 5.2 mM $TbCl_3$. A 10 kV voltage with reversed polarity was applied across the electrode. The sample solution prepared in running buffer was hydrodynamically injected for 5 seconds. Separated steroids were detected by a fixed 254 nm wavelength UV absorbance detector.

Figure 4A:
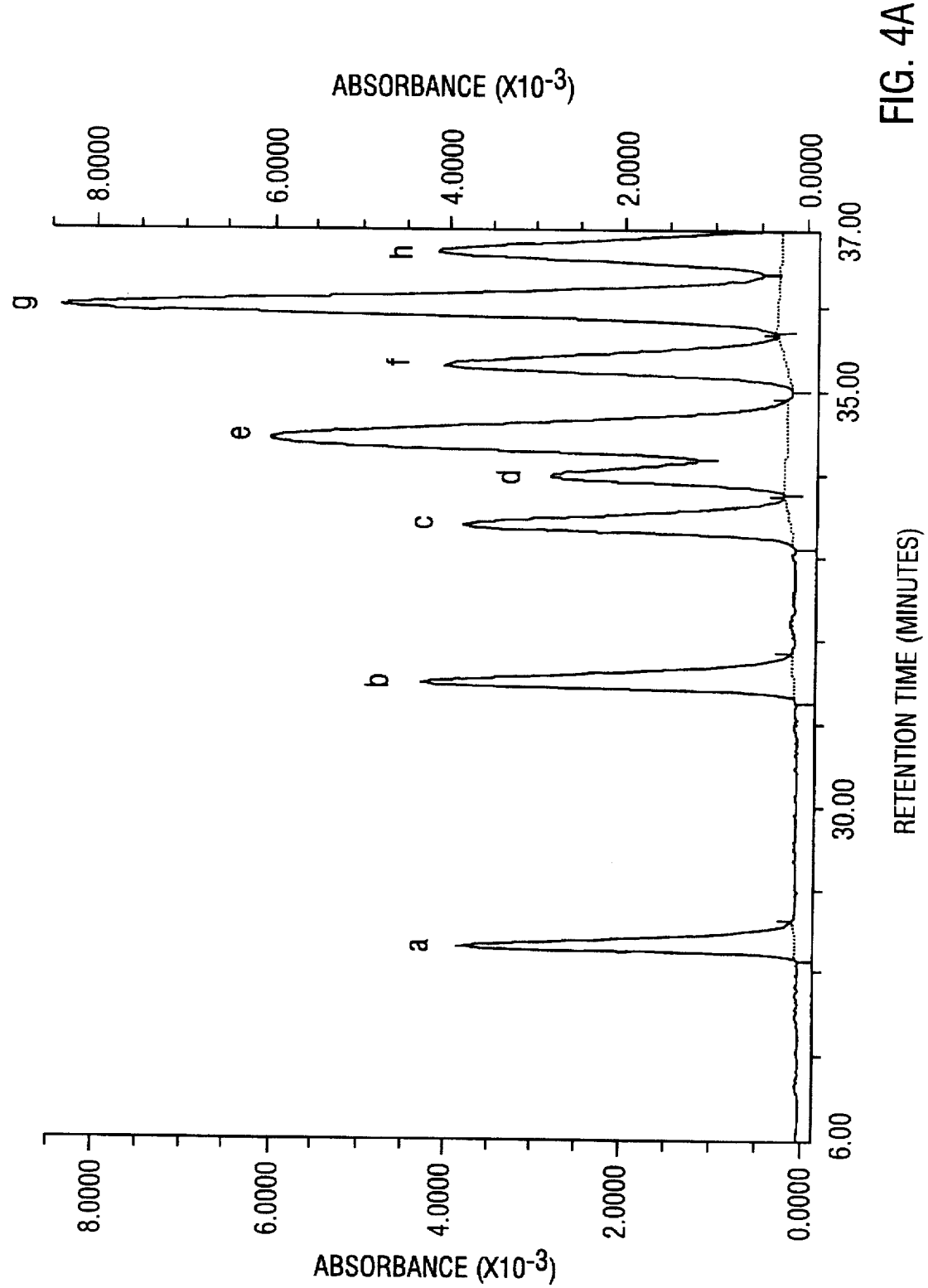
FIG. 4A and FIG. 4B show typical electropherograms obtained with (4A) and without (4B) $TbCl_3$ in the running buffer, clearly demonstrating the usefulness of terbium chloride in enhancing resolution. In 4A, the peaks represent compounds having retention times as follows: peak "a" is cortisone at 28.35 min; peak "b" is hydrocortisone at 31.54 min; peak "c" is 17-deoxycorticosterone at 33.42 min; peak "d" is fluoxymesterone at 34.01 min; peak "e" is testosterone at 34.46 min; peak "f" is dimethyltestosterone at 35.32 min; peak "g" is progesterone at 36.04 min; and peak "h" is testosterone propionate at 36.7 min In 4B, the peaks represent compounds having retention times as follows: cortisone at 8.26 min; hydrocortisone at 8.73 min; 17-deoxycorticosterone at 8.96 min; and the peaks at 9.07, 9.26 and 9.35 min represent an unresolved mixture of steroids.
Figure 4B:
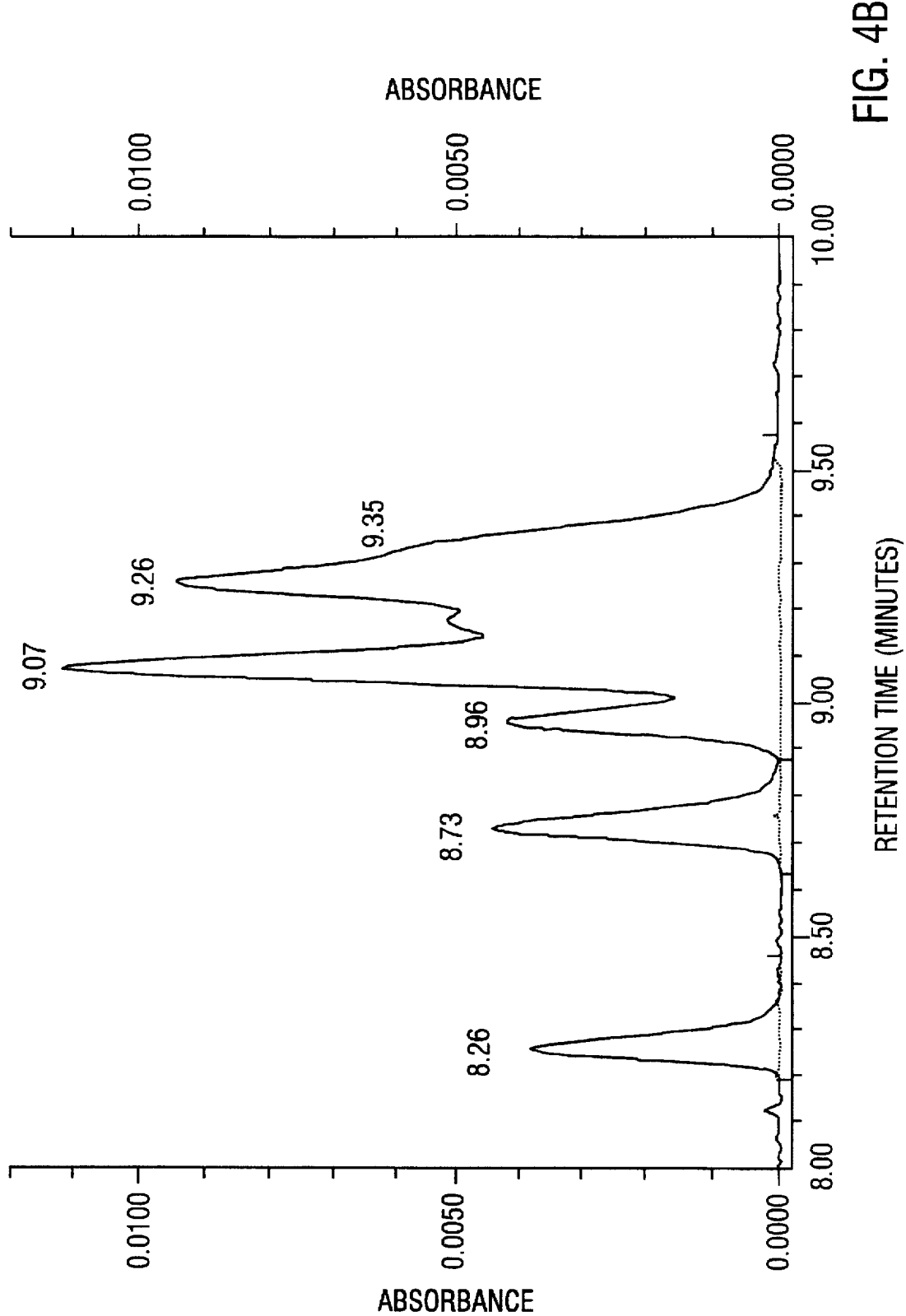

FIG. 4A and FIG. 4B show typical electropherograms obtained with (4A) and without $TbCl_3$ (4B) in the running buffer, clearly demonstrating the usefulness of terbium chloride in enhancing resolution as well as detection. The peaks in FIG. 4A represent compounds having retention times as follows: peak "a" is cortisone at 28.35 min; peak "b" is hydrocortisone at 31.54 min; peak "c" is 17-deoxycorticosterone at 33.42 min; peak "d" is fluoxymesterone at 34.01 min; peak "e" is testosterone at 34.46 min; peak "f" is dimethyltestosterone at 35.32 min; peak "g" is progesterone at 36.04 min; and peak "h" is testosterone propionate at 36.7 min. In 4B, the peaks represent compounds having retention times as follows: cortisone at 8.26 min; hydrocortisone at 8.73 min; 17-deoxycorticosterone at 8.96 min; and the peaks at 9.07, 9.26 and 9.35 min represent an unresolved mixture of steroids.

Although absorption was measured to detect the separated steroids in this example, one of skill in this art upon reading the present disclosure would realize that with a photoexcitation device capable of excitation at ~240 nm, terbium fluorescence could be measured concurrently with separation. Mohammad et al. (1993), which reference is incorporated herein by reference, reported the use of terbium for postcolumn detection and quantitation in HPLC to detect steroids possessing an α, β-unsaturated carbonyl group. Ideally, a KrF laser would be used for excitation at 240 nm and resultant fluorescence at ~547 nm would be measured. If such a laser were used, electropherogram data similar to that provided in FIG. 4A and 4B would be expected.

The negligible absorbance of terbium chloride in the ultraviolet region allowed a detection limit of at least 500 ng/ml for each of these steroids. These results of FIG. 4A and 4B suggest that not only is terbium providing an improved means of detection, but that its presence is also positively affecting the efficiency of separation of these structurally related steroids.

EXAMPLE 4

EU(III) as the Lanthanide Cation in CE

The present example provides the feasibility of using Eu(III) for energy transfer in the present methods.

Figure 6:
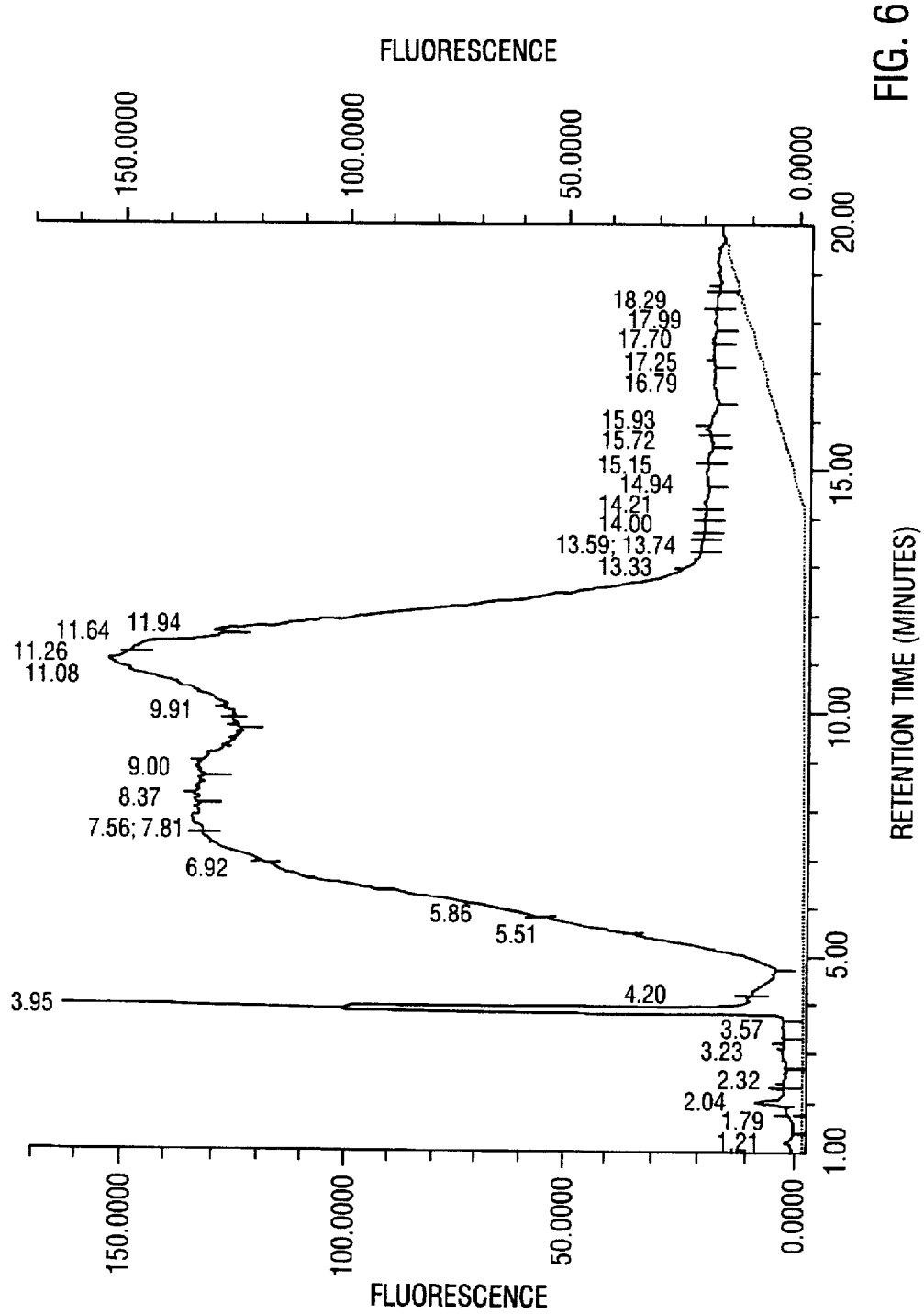
FIG. 6 demonstrates the detection of a complex formed between 4,4,4,-trisfluoro-1-(2-naphthyl)-1,3-butanedione and Eu(III) having a retention time of 3.95 min. The broad peak represents unresolved complexes.
Figure 7:
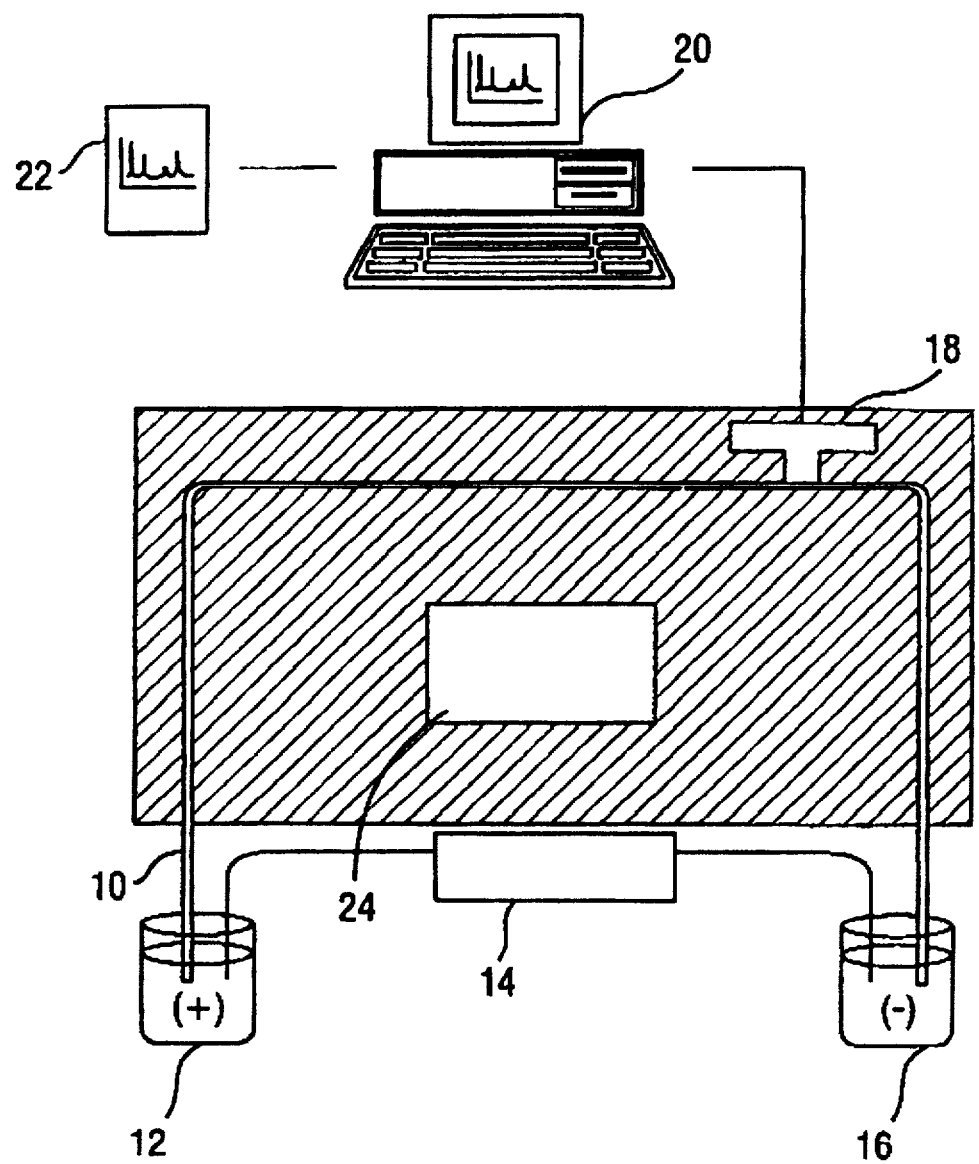
FIG. 7 shows a general schematic of a CE instrument adapted from Oda and Landers, 1994, including a capillary electrophoresis tube 10, a buffer reservoir 12, power supply 14, buffer reservoir 16, photoexcitation device and detector 18, data acquisition device 20, and resulting electropherogram 22, similar to that used in the methods of the present invention.

The separation and detection of a complex formed between 4,4,4,-trisfluoro-1-(2-naphthyl)-1,3-butanedione and europium is demonstrated in FIG. 6. The buffer was 0.1 mM naphthoyltrifluoroacetone (NTA), 20 mM MES (pH=6), and 10 mM DTAB. Electrophoresis was at 30 kV at 16° C. on a fused silica capillary of about 37 cm length. The sample was injected with 0.001M $EuCl_3.6H_2O$.

EXAMPLE 5

DNA Sequencing Using CE and a Lanthanide Cation Selected from Tb(III), Eu(III), Sm(III) and Dy(III)

The present inventors envision the methods provided herein to have utility in the determination of the nucleotide sequence of a DNA molecule. A DNA molecule may be immobilized via either its 3' or 5' end onto a solid support such as a bead, or the capillary electrophoresis tube itself. An exonuclease having activity for removing one nucleotide base at a time from the free end of the molecule is added. The released nucleotide may be detected by the methods of the present invention by having a lanthanide cation of the present invention in the buffer and detecting fluorescence resulting from photoexcitation of the nucleotide. The nucleotides A, C, G, and T would be expected to be distinguished because of their characteristic electrophoretic mobilities. Advantages of using the present methods include: i) the very small amount of material needed for analysis, ii) no pre- or postcolumn derivatization, and iii) no separate purification step.

EXAMPLE 6

Methods Development for CE Using a Lanthanide Cation for Concurrent Detection and Separation A generic development method for CE using a lanthanide cation for concurrent separation and detection of an analyte is as follows (adapted from a brochure by Beckman Instruments, Inc., Fullerton, Calif.).

Capillary zone electrophoresis (CZE) would be used for methods to detect compounds as described above. In addition, CZE can be used to detect proteins that bind a lanthanide cation and transfer energy. This method will also detect complexes formed, such as, sulfosalicylic acid/Tb(III) /protein.

Micellar electrokinetic capillary chromatography (MEKC) includes the use of compounds such as SDS or DTAB in the buffer to encase the lanthanide in a micelle, thereby reducing the quenching effect of water.

The following data should be gathered regarding the compound needing to be separated and concurrently detected by CE:

1. water solubility at different pH values,
2. solubility in aqueous solutions of methanol or acetonitrile (up to 25% MeOH or $CH_3CN$),
3. solubility in 100 mM SDS,
4. for proteins, solubility in 7M urea or a dispersant such as ethylene glycol,
5. pH stability,
6. thermal lability,
7. wavelength of maximum UV absorption, and
8. number of compounds in mixture and expected concentration of each.

Developing a Method for CZE

In this method, the processes for separating a new protein are reviewed. For starting conditions, a 75-cm capillary run at 25° C. at 20 kv with the detector set at 214 nm is used. A 1-second injection of a 1 mg/mL protein solution is carried out. A 100 mM buffer at the appropriate pH is used according to the following guidelines.

1. Acid stable—A buffer pH below the pI is used. Acid labile—A pH at least 1 unit above the pI is selected.
2. Solubility problem—A modifier such as urea or ethylene glycol is added.
3. Adsorption problem—An additive such as a sulfonic acid or a salt is used; or switch to a treated capillary.
4. Good efficiency, poor separation—The pH is adjusted.
5. Poor efficiency—The ionic strength of the buffer may be increased or a salt may be added in which the protein is stable.

Developing a Method for MEKC

MEKC is a good separation mechanism for small molecules. The upper molecular weight limit has not been established. However, proteins are not well separated by this technique.

Preferred starting conditions include 100 mM SDS at pH 7, 50 mM phosphate-borate buffer, after which adjustments in SDS concentration, pH, and organic modifier may be necessary. Some guidelines are as follows:

1. Long separation times, good resolution—The pH is increased, SDS concentration is decreased.
2. Long separation times, poor resolution—An organic modifier is used.
3. Short separation times, poor resolution—SDS concentration is increased.
4. Short separation times, moderate resolution—The pH is lowered and SDS concentration increased.

The use of the organic modifier is especially powerful in MEKC. Acetonitrile is the solvent of first choice since it has little impact on the electroosmotic force. Alcohols may also be useful, but the separation times can become lengthy.

Automated Methods Development

The P/ACE™ Systems 2050 and 2100 (Beckman Instruments, Inc., Fullerton, Calif.) have the capability of performing multiple separations with a variety of buffer solutions. This feature offers the possibility of automated, unattended methods development since fresh buffers in both the anode and cathode reservoirs can be used for each run. In this fashion, parameters such as pH, buffer concentration, additive type, and surfactant concentration, among other factors, can be optimized in a logical and systematic manner.

There are a few guidelines that will prove useful to ensure the efficient generation of applications information.

1. Perform a few preliminary separations to gain a general understanding of the problem.

2. Set the run time for the maximum expected separation time. For example, with MEKC, this would correspond to the highest surfactant concentration employed.
3. Some buffers such as phosphate permanently alter the wall chemistry; use these buffers last.
4. When switching from CZE to MEKC, allow sufficient time (at least 0.5 h) for the capillary to equilibrate with the surfactant solution.
5. Program a 0.1M sodium hydroxide wash between each run.
6. When determining the optimum temperature, allow sufficient time for thermal equilibration.
7. Modify only one experimental variable at a time.

The Beckman instructions 015-726434-A for eCAP™ SDS 14-200 Kit for capillary electrophoresis size separation of SDS proteins is incorporated by reference herein.

EXAMPLE 7

A Generic Kit for CE Separation and Concurrent Detection Using a Lanthanide Cation The present example provides a kit that may be used by a customer to develop a specific method for detection of an analyte. This can also be used as an example of how a method is developed in capillary electrophoresis since buffers covering the pH range are included.

A generic kit may contain the following items. The kit can be used for determining the best method to detect an analyte.

1. A capillary (either coated or uncoated depending upon the type of analyte that is to be detected). The length of the capillary depends on separation requirements. The length may vary from about 1 cm to over 100 cm. Preferred lengths are ~27 cm, ~47 cm, or ~57 cm.
2. A set of the following buffers covering the pH range of 3-10.
   a) 50 mM citric acid, pH 3.0
   b) 50 mM acetate, pH 4.5
   c) 20 mM MES (morpholino ethane sulfonic acid), pH 6.0
   d) 50 mM TRIS, pH 8.0
   e) 20 mM sodium carbonate, pH 10.0
   f) 10 mM EDTA/Tb, pH 12.0
3. Wash buffers
   a) 0.1M HCl
   b) 0.1M NaOH
4. Detection reagents
   a) 100 mM p-aminosalicylic acid sodium salt (PAS)
   b) 100 mM lanthanide salt, such as $TbCl_3$ or $Tb(NO_3)$ or $EuCl_3$ General Procedure The method development will depend on the type of compound to be detected. The compound can range from a small molecule to a protein or DNA capable of transferring energy to a lanthanide cation of the present invention either directly or in a ternary complex with a molecule facilitating energy transfer. If the molecule can transfer energy to Tb(III) as determined experimentally, use Procedure A. If the compound is not capable of transferring energy to Tb(III), use procedure B. Procedure B is useful for detecting compounds, such as citric acid, EDTA, EGTA, oxalate, and other poly acids.

Procedure A

1. The run buffer is prepared by diluting the 100 mM Tb(III) solution to 10 mM with the appropriate buffer.

(note: Buffer that has a pH<7.0 can be used directly, however if the pH>7.0 then the buffer containing EDTA must be used).
2. Equilibrate the capillary with run buffer for 10 minutes.
3. Inject the solution containing the sample into the capillary and apply voltage (note: the voltage may range from 1-30 kv)
4. Excitation wavelength will be dependent on availability of specific lasers.

Procedure B

1. The run buffer is prepared by adding 10 mM of PAS to the appropriate buffer.
2. Add Tb(III) (1 mM) to the sample and adjust the buffer to approximately pH 6.5.
3. Inject the solution into the capillary and apply voltage as above.
4. Excitation wavelength will be at 325 nm because the PAS absorbs at this wavelength.

EXAMPLE 8

CE Separation and Concurrent Detection For Polyaminopolycarboxylic Acids

The present example provides materials and methods for a kit for the analysis of polyaminopolycarboxylic acids, such as, for example, EDTA, citric acid, oxalate or DTPA.

The components of a kit may contain:
a) a capillary column, preferably made from fused silica;
b) a running buffer, preferably 5 mM p-aminosalicylic acid and 20 mM $Na_2CO_3$ (pH of about 12);
c) a lanthanide cation, preferably 0.01M $TbCl_3$ in water;
d) wash buffer 1, preferably 0.1N HCl; and
e) wash buffer 2, preferably an alkaline metal hydroxide such as 0.1N NaOH or KOH.

To the sample containing a polyaminopolycarboxylic acid, 1 mL of lanthanide cation is added. The sample is then applied to a capillary column in an electrophoresis apparatus.

EXAMPLE 9

CE Separation and Concurrent Detection For Aromatic Donors

The present example provides materials and methods for a kit for the analysis of aromatic donors. For example, phenylketonuria may be diagnosed by the determination of increased levels of phenylalanine over a control level. A control level is about 4 mg phenylalanine/dl serum. Salicylate poisoning may be analyzed by the determination of salicylic acid metabolites and hydroxyindoles.

The components of a kit may contain:
a) a capillary column, preferably, made from fused silica;
b) a running buffer containing a lanthanide cation, preferably 0.002M Tb(III)-EDTA and 20 mM $Na_2CO_3$ (pH of about 10);
c) wash buffer, preferably an alkaline metal hydroxide such as 0.1N NaOH or KOH.

A sample containing an aromatic donor is directly injected onto the capillary column.

EXAMPLE 10

CE Separation and Concurrent Detection for Steroids

The present example provides materials and methods for a kit for the analysis of steroids, such as, for example, for use in analyses of athletes, or for congenital adrenal hyperplasia.

The components of a kit may contain:

a) a capillary column, preferably, made from fused silica, surface modified or neutral, and having a length of about 20–50 cm, more preferably, about 37 cm;

b) a running buffer, preferably 100 mM SDS, 20% v/v acetonitrile and 20 mM morpholino ethane sulfonic acid (MES), and 0.01M $TbCl_3$;

c) wash buffer, preferably 0.1N HCl; and d) diluent buffer, preferably, morpholino ethane sulfonic acid at a pH of about 4.

A sample containing a steroid is diluted with diluent buffer, ultracentrifuged and directly applied to a capillary column in an electrophoresis apparatus.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the composition, methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

Bailey et al., *Analyst*, 109 (1984) 1449.

Bailey et al. *Anal. Chim. Acta*, 201 (1987) 335.

Burton et al., *J. Chromatogr. Sci.*, 24 (1986) 347–351.

Charles et al., *J. Inorg. Nucl. Chem.*, 28 (1966) 527.

Cheng et al., *Science*, 242 (1988) 562.

Christopoulos et al., *Anal. Chem.*, 64 (1992) 342.

Cohen et al., *Anal. Chem.*, 59 (1987) 1021–1027.

Crosby et al., *J. Phys. Chem.*, 66 (1962) 2493.

Escabi-Perez et al., *J. Am. Chem. Soc.*, 99(24) (1977) 7749.

Eskola et al., *Clin. Chem.*, 29 (1983) 1777.

Evans, in *Biochemistry of Lanthanides*, Vol. 1 and 2, Plenum Press, NY, 1990.

Foret et al., *Electrophoresis*, 11 (1990) 1872.

Gassmann et al., *Science*, 230 (1985) 813.

Georges, *Analyst*, 118 (1993) 1481–1486.

Gross et al., *J. Chromatogr.*, 480 (1989) 169.

Guttman et al., *Anal. Chem.*, 63 (1991) 2038.

Hemmilä, et al., European Patent No. 0,064,484, 1982.

Hemmilä et al., *Anal. Biochem.*, 137 (1984) 335.

Hernandez, L. et al., "Laser-Induced Fluorescence Detection for Capillary Electrophoresis" in *Capillary Electrophoresis* ed. N. A. Guzman, Marcel Dekker, Inc. N.Y., N.Y. 1993

Honda, et al. *J. Chromatogr.*, 588 (1991) 327.

Honda et al., *Carbohydr. Res.*, 215 (1991) 193.

Issaq et al., *J. Liq. Chromatogr.*, 15(6–7) (1992) 1129.

Janini et al., *J. Liq. Chromatogr.*, 24 (1987) 15.

Jorgenson et al., *J. High Resolut. Chromatogr. Commun.*, 4 (1981) 230.

Kallistratos et al., *Chimika Chronika, New Series*, 11 (1982) 249.

Karovicova et al., *Nahrung*, 34 (1991) 765.

Kuhr et al., *Anal. Chem.* 60 (1988) 1832.

Kuhr et al., *Anal. Chem.* 60 (1988) 2642.

Latva et al., *Analyst*, 120:367 (1995).

Leung et al., *Biochem. Biophys. Res. Commun.*, 75 (1977) 149.

Macek et al., *J. Chromatogr*, 593 (1992) 297.

McCormick, *Anal. Chem.*, 60 (1988) 2322.

Mikola et al., Compound, WO Patent 03698, 1984.

Miller et al., *Biochem. Med.*, 13 (1975) 98.

Mohammad et al., *Anal. Chem.*, 65 (1993) 2346.

Mosher, *Electrophoresis*, 11(9) (1990) 765.

Nickerson et al., *J. High Resolution Chromatogr Commun.*, 10 (1988) 533.

Nickerson et al., *J. High Resolution Chromatogr Commun.*, 11 (1988) 878.

Nielen, *J. Chromatogr.*, 608 (1992) 85–92.

Nishi et al., *J. of Chromatogr.*, 13 (1990) 279–295.

Oda et al., "Introduction to Capillary Electrophoresis," in: *Handbook of Capillary Electrophoresis*, J. P. Landers, ed., CRC Press, Boca Raton, Fla. (1994) Chapter 2, pg. 15.

Olefirowicz, et al., *Anal. Chem.*, 62 (1990) 1872.

Otsuka et al., *Nippon Kagaku Kaishi*, No. 7 (1986) 950–955.

Pettersson et al., *Clin. Chem.*, 29 (1983) 60.

Schreurs et al., *Analytica Chimica Acta*, 262 (1992) 201.

Siepak, *Analyst*, 114 (1989) 529.

Siepak, J., *Anal. Chim. Acta*, 201 (1989) 143.

Sinha, S. P., editor, *Systematics and the Properties of the Lanthanides*, NATO ASI series, D. Reidel Publishing Company, Boston, Mass., 1982

Soini et al., *CRC Critical Reviews in Analytical Chemistry*, vol. 18(2) (1987) 105–154.

Stevenson, *American Laboratory*, 26(18) (1994) 29.

Swerdlow et al., *Anal. Chem.*, 63 (1991) 2835.

Szejtli et al., 'Cyclodextrin use in separations,' in "Ordered Media in Chemical Separations," W. L. Hinze, D. W. Armstrong, eds., ACS Symposium Series 342, American Chemical Society, Washington D.C. (1987) pp. 200–217.

Terabe et al., *J. Chromatogr.*, 545 (1991) 359–368.

Terabe et al., *Anal. Chem.*, 56 (1984) 111.

Tobita et al., *J. Phys. Chem.* 89 (1985) 5649.

Tran et al., *Anal. Chem.* 62(8) (1990) 835.

Wallingford et al., *Anal. Chem.*, 60 (1988) 258.

Weissman, *J. Chem. Phys.*, 10 (1942).

Whan et al., *J. Mol. Spectrosc.* 8 (1962) 315.

Wu et al., *J. Chromatogr.*, 480 (1989) 141.

What is claimed is:

1. A method of separating and concurrently detecting an organic analyte having an absorption spectrum from about 230 nm to 400 nm in a sample, the method comprising:

introducing at least a portion of the sample to a capillary electrophoresis apparatus that contains an aqueous running buffer and a capillary electrophoresis column, wherein the sample is introduced to the capillary electrophoresis column without prior derivatization, and wherein the sample enters the capillary electrophoresis column with a lanthanide cation selected from the group consisting of Tb(III), Eu(III), Dy(III), and Sm(III) in an amount that will promote energy transfer;

applying a voltage to the capillary electrophoresis apparatus to electrophoretically separate the analyte of the sample; and, concurrently detecting the separated analyte by measuring lanthanide ion fluorescence resulting from photoexcitation of the analyte.

2. The method of claim 1 where the organic analyte has an excited energy level sufficient to transfer energy directly to the lanthanide cation.

3. The method of claim 2 where the applying step is further carried out with a molecule that facilitates energy transfer for ease of photoexcitation and detection.

4. The method of claim 3 where the organic analyte is selected from the group consisting of a polycarboxylic acid and an amino acid.

5. The method of claim 4 where the polycarboxylic acid is selected from the group consisting of EDTA, EGTA, citric acid, 1,2 diaminopropane tetraacetic acid, trans 1,2 cyclohexanediaminetetraacetic acid and hexamethylene diaminetetraacetic acid.

6. The method of claim 2 where the organic analyte has a functional group selected from the group consisting of an α,β unsaturated carbonyl group, an α-keto acid, an aromatic group, an indole carboxylic acid, and a β-diketone group.

7. The method of claim 2 where the organic analyte is selected from the group consisting of salicylic acid, p-aminosalicylic acid, sulfosalicylic acid, and indole carboxylic acid.

8. The method of claim 2 wherein the organic analyte is selected from the group consisting of testosterone, mesterone, bolasterone, cortisone, progesterone, hydrocortisone, corticosterone, and fluoxymesterone.

9. The method of claim 2 wherein the organic analyte includes a moiety selected from the group consisting of a pyrrole, furan, thiophene, phenyl, biphenyl, pyridine, pyrimidine, pyrazine, quinoline, phenanthroline, purine, porphyrin and phosphonimido moiety.

10. The method of claim 1 where the organic analyte does not have an excited energy level that will transfer energy directly to the lanthanide cation and the applying step is further carried out with a molecule that facilitates energy transfer to the lanthanide cation.

11. The method of claim 3 or 10 where the molecule that facilitates energy transfer has a group selected from the group consisting of an α,β unsaturated carbonyl group, an α-keto acid, an aromatic group, an indole carboxylic acid, and a β-diketone group.

12. The method of claim 3 or 10 where the molecule that facilitates energy transfer is selected from the group consisting of ethylenediamine tetraacetic acid (EDTA), ethyleneglycol-bis-(β-aminoethylether)-N,N,N'N'-tetraacetic acid (EGTA), citric acid, salicylic acid, p-aminosalicylic acid, sulfosalicylic acid, and indolecarboxylic acid.

13. The method of claim 10 where the organic analyte is selected from the group consisting of a crown ether and a cyclodextran.

14. The method of claim 1 wherein the lanthanide cation is Tb(III).

15. The method of claim 1 wherein the lanthanide cation is Eu(III).

16. The method of claim 1 wherein the applying step is further carried out with an agent for solubilizing the lanthanide cation.

17. The method of claim 16 wherein the agent is selected from the group consisting of EDTA, EGTA, citric acid, 1,2 diaminopropane tetraacetic acid, trans-1,2 cyclohexane diaminetetraacetic acid and hexamethylene diamine tetraacetic acid.

18. The method of claim 16 wherein the agent is EDTA.

19. The method of claim 1 wherein the applying step is carried out with an aqueous running buffer selected from the group consisting of morpholinoethanesulfonic acid (MES), morpholinopropanesulfonic acid (MOPS), tris (hydroxymethyl)-aminomethane (TRIS)-citric acid, 4-(2-hydroxyethyl)-1-piperazine ethanesulfonic acid (HEPES), EDTA, sodium carbonate with EDTA, citric acid and boric acid.

20. The method of claim 1 wherein the detecting is carried out by laser-induced luminescence.

21. The method of claim 1 wherein the detecting is carried out by time-resolved luminescence.

22. The method of claim 1 wherein the applying step is further carried out with a micellar medium.

23. The method of claim 22 where the micellar medium is selected from the group consisting of dodecyl trimethylammonium bromide (DTAB), sodium dodecyl sulfate (SDS), α-[4-(1,1,3,3-tetramethylbutyl)phenyl]-ω-hydroxypoly(oxy-1,2-ethanediyl) (Triton X), polyoxyethylene (20) sorban monolaurate (Tween), and polyoxyethylene (23) lauryl ether (Brij-35).

24. A method of separating and concurrently detecting an organic analyte having an absorption spectrum from about 230 nm to 400 nm in a sample, the method comprising:

introducing at least a portion of the sample to a capillary electrophoresis apparatus that contains an aqueous running buffer and a capillary electrophoresis column, wherein said aqueous running buffer contains a lanthanide cation selected from the group consisting of Tb(III), Eu(III), Dy(III), and Sm(III) in an amount that will promote energy transfer, and wherein the sample is introduced to the capillary electrophoresis column without prior derivatization;

applying a voltage to the capillary electrophoresis apparatus to electrophoretically separate the analyte; and, concurrently detecting the separated analyte by measuring lanthanide ion fluorescence resulting from photoexcitation of the analyte.

25. A method of separating and concurrently detecting an organic analyte having an absorption spectrum from about 230 nm to 400 nm in a sample, the method comprising:

introducing at least a portion of the sample to a capillary electrophoresis apparatus that contains an aqueous running buffer and a capillary electrophoresis column, wherein the sample is aqueous and introduced to the capillary electrophoresis column without prior derivatization, and wherein the sample enters the capillary electrophoresis column with a lanthanide cation selected from the group consisting of Tb(III), Eu(III), Dy(III), and Sm(III) in an amount that will promote energy transfer;

applying a voltage to the capillary electrophoresis apparatus to electrophoretically separate the analyte; and, concurrently detecting the separated analyte by measuring lanthanide ion fluorescence resulting from photoexcitation of the analyte.

* * * * *